（12） United States Patent
Epstein et al.

(10) Patent No.: US 6,949,661 B2
(45) Date of Patent: Sep. 27, 2005

(54) 3-SUBSTITUTED-3-(SUBSTITUTEDSULFONYL OR SULFANYL) PYRROLIDINE-2,5-DIONES USEFUL FOR INHIBITION OF FARNESYL-PROTEIN TRANSFERASE

(75) Inventors: Joseph William Epstein, Monroe, NY (US); Semiramis Ayral-Kaloustian, Tarrytown, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 180 days.

(21) Appl. No.: 10/672,849

(22) Filed: Sep. 26, 2003

(65) Prior Publication Data

US 2004/0063971 A1 Apr. 1, 2004

Related U.S. Application Data

(62) Division of application No. 10/227,215, filed on Aug. 23, 2002, now Pat. No. 6,740,675.
(60) Provisional application No. 60/314,585, filed on Aug. 24, 2001.

(51) Int. Cl.$^7$ ............................................. C07D 207/00
(52) U.S. Cl. .................................................... 548/530
(58) Field of Search ........................................ 548/530

(56) References Cited

FOREIGN PATENT DOCUMENTS

| WO | WO 95/24400 | 9/1995 |
|---|---|---|
| WO | WO 97/36605 | 10/1997 |
| WO | WO 98/07692 | 2/1998 |
| WO | WO 99/05117 | 2/1999 |
| WO | WO 01/85685 | 11/2001 |

OTHER PUBLICATIONS

J.L. Bos, Cancer Res., 1989, 49, 4682.
P.J. Casey, P.A. Solski, C.J. Der, J.E. Buss, Proc. Natl. Acad. Sci. U.S.A., 1989, 86, 8323.
J.F. Hancock, H. Paterson, C.J. Marshall, Cell, 1990, 63, 133.
Zask, et al., J. Med. Chem., 1990, 33, 1418–1423.
P. Skehan, R. Storeng, D. Scudiero, A. Monks, J. McMohan, D. Vistica, J. Warren, J. Bokesh, S. Kenney, M.R. Boyd, J. Natl. Cancer Instit., 1990, 82(13), 1107–1112.
L.V. Rubinstein, R.H. Shoemaker, K.D. Paull, R.M. Simon, S. Tosini, P. Skehan, D.A. Scudiero, A. Monks, M.R. Boyd, J. Natl. Cancer Instit., 1990, 82(13), 1113–1118.
J.F. Moomaw, P.J. Casey, J. Biol. Chem., 1992, 267, 17438–17443.
M.A. Garcia, et al., J. Biol. Chem., 1993, 268, 18415–18420.
G.L. Bolton, J.S. Sebolt–Leopold, J.C. Hodges; Annu. Rep. Med. Chem., 1994, 29, 165.
R.J.A. Grand in "New Molecular Targets in Cancer Chemotherapy", J.D. Kerr and P. Workman, Eds. CRC Press, Boca Raton, FL., 1994, p. 97.
G.L. James, M.S. Brown, J.L. Goldstein, Methods in Enzymology, 1995, 255, 38–46.
M.R. Boyd, K.D. Paull, Drug Development Res., 1995, 34, 91–109.
S.P. Fricker, R.G. Buckley, Anticancer Research, 1996, 16, 3755–3760.
S. Ayral–Kaloustian, J.S. Skotnicki, Annu. Rep. Med. Chem., 1996, 31, 171.
T.M. Williams, Exp. Opin. Ther. Patents, 1998, 8, 553.
SCH–66336, Pharmaprojects, 1998, No. 5128.
R–115777, Pharmaprojects, 1998, No. 5532.

Primary Examiner—Taofiq Solola
Assistant Examiner—Robert Shiao
(74) Attorney, Agent, or Firm—Daniel B. Moran

(57) ABSTRACT

The invention relates to compounds of Formula (I), to processes for their preparation and pharmaceutical compositions thereof, that inhibit the Ras farnesyl-protein transferase enzyme (FPTase), and may be used as an alternative to, or in conjunction with, traditional cancer therapy for the treatment of ras oncogene-dependent tumors, such as cancers of the pancreas, colon, bladder, and thyroid.

Formula (I)

$$R_1-S(O)_m-\underset{\underset{O}{\|}}{\overset{(CH_2)_n \equiv\!\equiv\!\equiv R_2}{\underset{\|}{\overset{\|}{C}}}}\hspace{-1.5em}\begin{array}{c}\\ \\ NH\end{array}$$

6 Claims, No Drawings

3-SUBSTITUTED-3-(SUBSTITUTEDSULFONYL OR SULFANYL) PYRROLIDINE-2,5-DIONES USEFUL FOR INHIBITION OF FARNESYL-PROTEIN TRANSFERASE

This application is a divisional application of application Ser. No. 10/227,215, filed Aug. 23, 2002, now U.S. Pat. No. 6,740,675, which claims benefit of prior U.S. Provisional Application No. 60/314,585 filed Aug. 24, 2001. These applications are herein incorporated by reference in their entireties.

FIELD OF THE INVENTION

The present invention relates to a novel series of 3-substituted-3-(substitutedsulfonyl)pyrrolidine-2,5-diones, and 3-substituted-3(substitutedsulfanyl)pyrrolidine-2,5-diones, to their use in cancer therapy, to pharmaceutical compositions containing them, and to a process for their preparation. The compounds are inhibitors of Ras FPTase, and may be used as an alternative to, or in conjunction with, traditional cancer therapy for treating ras oncogene-dependent tumors, such as cancers of the pancreas, colon, bladder, and thyroid. Compounds in the invention may also be useful for controlling metastasis, suppressing angiogenesis, inducing apoptosis, and in treating Ras-associated proliferative diseases other than cancer, such as restenosis, neuro-fibromatosis, endometriosis, and psoriasis. These compounds may also inhibit prenylation of proteins other than Ras, and thus may be effective in the treatment of diseases associated with other prenyl modifications of proteins.

BACKGROUND OF THE INVENTION

Mammalian H-, K-, and N-Ras proteins, encoded by H-, K-, and N-ras proto-oncogenes, respectively, are 21 kD GTP-binding proteins which possess intrinsic GTPase activity and play a fundamental role in cell proliferation and differentiation (G. L. Bolton, J. S. Sebolt-Leopold, and J. C. Hodges, *Annu. Rep. Med. Chem.*, 1994, 29, 165; R. J. A. Grand in "New Molecular Targets in Cancer Chemotherapy" J. D. Kerr, and P. Workman, Eds., CRC Press, Boca Raton, Fla., 1994, p. 97). Specific mutations in the ras gene impair GTPase activity of Ras, leading to uninterrupted growth signals and to the transformation of normal cells into malignant phenotypes. Mutant ras oncogenes are found in approximately 25% of all human cancers, including 90% of pancreatic, 50% of colon, and 50% of thyroid tumors (J. L. Bos, *Cancer Res.*, 1989, 49, 4682). It has been shown that normal cells transfected with mutant ras gene become cancerous and that unfarnesylated, cytosolic mutant Ras protein does not anchor in cell membranes and cannot induce this transformation (J. F. Hancock, H. Paterson, and C. J. Marshall, *Cell*, 1990, 63, 133). Posttranslational modification and plasma membrane association of mutant Ras is essential for this transforming activity. The first and required step in the processing of Ras is farnesylation at the cysteine residue of its carboxyl terminal motif, CAAX (C=Cys-186, A=aliphatic amino acid, X=usually methionine, serine or glutamine). Since its identification, the enzyme farnesyl-protein transferase (FPTase) that catalyzes this first processing step has emerged as a promising target for therapeutic intervention (H.-W. Park, S. R. Boduluri, J. F. Moomaw, P. J. Casey, and L. S. Beese, *Science*, 1997, 275, 1800; P. J. Casey, P. A. Solski, C. J. Der, and J. E. Buss, *Proc. Natl. Acad. Sci. U.S.A.*, 1989, 86, 8323; S. Ayral-Kaloustian and J. S. Skotnicki, *Annu. Rep. Med. Chem.*, 1996, 31, 165, and references therein). Major milestones have been achieved with small molecules, such as mimics of the tetrapeptide CAAX and analogs of farnesyl pyrophosphate, that show efficacy without toxicity in vitro as well as in mouse models bearing ras-dependent tumors or human xenografts with H-, N-, or K-ras mutations (S. Ayral-Kaloustian and J. S. Skotnicki, *Annu. Rep. Med. Chem.*, 1996, 31, 165, and references therein; T. M. Williams, *Exp. Opin. Ther. Patents*, 1998, 8, 553, and references therein). Several low-molecular weight compounds that inhibit FPTase have entered Phase I trials in humans (SCH-66336, *Pharmaprojects*, 1998, No. 5128; R-115777, *Pharmaprojects*, 1998, No. 5532).

Accordingly, there is still a need for drugs for treating and preventing cancer. In particular, there is a need for drugs which inhibit or treat the growth of tumors expressing an activated Ras oncogene and which include cancers of the pancreas, colon, bladder and thyroid.

BRIEF SUMMARY OF THE INVENTION

The present invention discloses compounds represented by Formula (I):

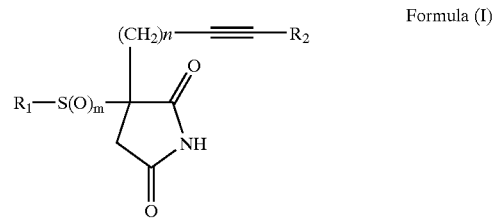

Formula (I)

wherein:
$R_1$ is a moiety

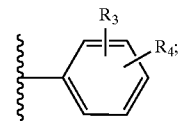

$R_2$ is a moiety

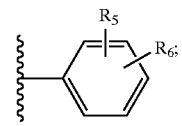

n is an integer of 1 and 3–9;
m is an integer of 0 or 2;
$R_3$ and $R_4$ are independently selected from the group consisting of hydrogen, alkyl of 1 to 10 carbon atoms, alkoxy of 1 to 10 carbon atoms, halogen, nitro, trifluoromethoxy, phenoxy optionally mono or di substituted, and benzyloxy optionally mono or di substituted;
$R_5$, and $R_6$, are independently selected from the group consisting of hydrogen, alkyl of 1 to 10 carbon atoms, halogen, nitro, phenyl optionally mono or di-substituted, phenoxy optionally mono or di-substituted, trifluoromethyl, trifluoromethoxy, and methanesulphonyl. or a pharmaceutically acceptable salt thereof.

Among the preferred groups of compounds of Formula (I) of this invention including pharmaceutically acceptable salts thereof are those in the subgroups below, wherein the other variables of Formula (I) in the subgroups are as defined above wherein:

a.) $R_1$ is 4-methoxyphenyl and $R_2$ is 4-chlorophenyl;
b.) n is 3 and m is 2;

Specifically preferred compounds of this invention according to Formula (I) for treating or controlling ras oncogene-dependent tumors and associated proliferative diseases in warm-blooded animals preferably mammals, most preferably humans in need thereof are the following compounds or a pharmaceutically acceptable salt thereof:
3-[5-(4-Chlorophenyl)pent-4-ynyl]-3-(4-methoxybenzene-sulfonyl)-pyrrolidine-2,5-dione; and
3-[3-(4-Chlorophenyl)prop-2-ynyl]-3-(4-methylbenzene-sulfonyl)-pyrrolidine-2,5-dione.

It is understood that the definition of compounds of Formula (I) when $R_1$, $R_2$, $R_3$, $R_4$, $R_5$, or $R_6$ contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of Formula (I).

Pharmaceutically acceptable salts of the compounds in this invention may be formed with bases such as alkali metals (Na, K, Li) or alkaline earth metals (Ca or Mg).

For the compounds of Formula (I) defined above and referred to herein, unless otherwise noted, the following terms are defined:

Halogen, as used herein means chloro, fluoro, bromo and iodo.

Alkyl as used herein means a branched or straight chain having from 1 to 10 carbon atoms and more preferably from 1 to 6 carbon atoms. Exemplary alkyl groups include methyl, ethyl, propyl, isopropyl, butyl, isobutyl, t-butyl, pentyl and hexyl.

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Phenyl as used herein refers to a 6-membered aromatic ring, optionally substituted. Preferably, the phenyl ring is optionally mono or di substituted.

Where a group, e.g. phenyl, phenoxy, benzyloxy is described as optionally mono or di substituted, the substituents are preferably independently selected from alkyl of 1 to 10 carbon atoms, alkoxy of 1 to 10 carbon atoms, halogen, nitro, trifluoromethyl, trifluoromethoxy, methanesulphonyl, phenyl, phenoxy, and benzyloxy. Said phenyl, phenoxy and benzyloxy groups may themselves be mono or disubstituted by substituents independently selected from alkyl of 1 to 10 carbon atoms, alkoxy of 1 to 10 carbon atoms, halogen, nitro, trifluoromethyl, trifluoromethoxy, methanesulphonyl, and phenyl.

Additionally, this invention provides a method of treatment, by administration of an effective amount of compounds of Formula (I), of ras oncogene-dependent tumors, which include cancers of the pancreas, colon, bladder, and thyroid; a method of controlling metastasis, suppressing angiogenesis, and inducing apoptosis; a method of treating Ras-associated proliferative diseases other than cancer, which include restenosis, neuro-fibromatosis, endometriosis, and psoriasis in a mammal in need thereof. The compounds of Formula (I) may also inhibit prenylation of proteins other than Ras, and thus provide a method of treatment of diseases associated with other prenyl modifications of proteins.

The compounds of Formula (I) inhibit farnesyl-protein transferase and the farnesylation of the oncogene protein Ras. Thus, this invention further provides a method of inhibiting farnesyl protein transferase, (e.g., Ras farnesyl protein transferase) in mammals, especially humans, by the administration of an effective amount of the compounds of Formula (I). The administration of the compounds of this invention to patients, to inhibit farnesyl protein transferase, is useful in the treatment of the cancers and other diseases described below.

This invention provides a method for inhibiting or treating the abnormal growth of cells, including transformed cells by administering an effective amount of a compound of Formula (I). Abnormal growth of cells refers to cell growth independent of normal regulatory mechanisms (e.g., loss of contact inhibition). This includes abnormal growth of tumor cells (tumors) expressing an activated Ras oncogene; tumor cells in which the Ras protein is activated as a result of oncogenic mutation in another gene; and benign and malignant cells of other proliferative diseases in which aberrant Ras activation occurs.

This invention also provides a method for inhibiting or treating tumor growth by administering an effective amount of a compound of Formula (I), described herein, to a mammal (e.g., a human) in need of such treatment. In particular, this invention provides a method for inhibiting or treating the growth of tumors expressing an activated Ras oncogene by administration of an effective amount of a compound of Formula (I). Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

Further, this invention also provides a method for inhibiting or treating proliferative diseases, both benign and malignant, wherein Ras proteins are aberrantly activated as a result of oncogenic mutation in other genes-i.e., the Ras gene itself is not activated by mutation to an oncogenic form-with said inhibition or treatment being accomplished by the administration of an effective amount of a compound of Formula (I), to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the compounds of Formula (I).

Additionally, this invention provides a method of inhibition or treating the abnormal growth of cells, by administration of an effective amount of compounds of Formula (I), of ras-oncogene-dependent tumors, which tumors include cancers of the pancreas, colon, bladder, and thyroid. Without wishing to be bound by theory, these compounds may function through the inhibition of G-protein function, such as ras p21, by blocking G-protein isoprenylation, thus making them useful in the treatment of proliferative diseases such as tumor growth and cancer. Without wishing to be bound by theory, compounds of Formula (I) inhibit Ras farnesyl-protein transferase, and thus antiproliferative activity of ras-transformed cells and other prenyl modifications of proteins.

In another aspect, the invention provides a process for the preparation of a compound of Formula (I):

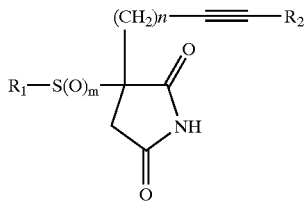

Formula (I)

wherein:

$R_1$ is a moiety

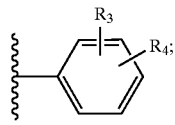

$R_2$ is a moiety

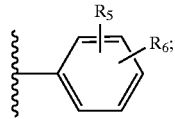

n is an integer of 1 and 3–9;

m is an integer of 0 or 2;

$R_3$ and $R_4$ are independently selected from the group consisting of hydrogen, alkyl of 1 to 10 carbon atoms, alkoxy of 1 to 10 carbon atoms, halogen, nitro, trifluoromethoxy, phenoxy optionally mono or di substituted, and benzyloxy optionally mono or di substituted;

$R_5$, and $R_6$, are independently selected from the group consisting of hydrogen, alkyl of 1 to 10 carbon atoms, halogen, nitro, phenyl optionally mono or di-substituted, phenoxy optionally mono or di-substituted, trifluoromethyl, trifluoromethoxy, and methanesulphonyl.

or a pharmaceutically acceptable salt thereof, which comprises
reacting a compound of the formula

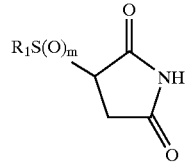

with an alkyne of the formula

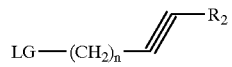

wherein LG is a leaving group
in the presence of a base to give a compound of Formula (I)
or a pharmaceutically acceptable salt thereof.

DETAILED DESCRIPTION OF THE INVENTION

The present invention also provides a process for the preparation of compounds of Formula (I).

Scheme I

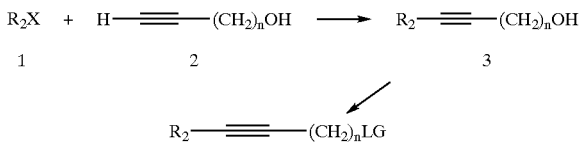

4a LG is p-toluenesulfonyloxy
4b LG is iodo
4c LG is bromo

Referring to Scheme I, reaction of halide 1 where $R_2$ is hereinbefore defined and X is bromo or iodo with alcohol 2 where n is hereinbefore defined in the presence of a catalytic amount of a palladium(II) reagent, dichlorobis(triphenylphosphine)palladium(II), and the like and a catalytic amount of a copper(I) reagent, copper(I) iodide affords alkyne 3. The reaction is performed in the presence of one or more equivalents of a secondary or tertiary amine which include diethylamine or triethylamine and the like. The secondary or tertiary amine may optionally be used as solvent or a halocarbon which includes chloroform may be employed as solvent. Reactions are performed at room temperature to about 80° C., with reaction times of 1 hr to 2 days. Reaction of alkyne 3 with p-toluenesulfonyl chloride (PTSCl) in dichloromethane and the like in the presence of a base selected from N,N-dimethylaminopyridine and triethylamine and the like at about 0° C. to about 30° C., for about 1 to 6 hours gives substituted alkyne 4a where the leaving group (LG) is p-toluenesulfonyloxy. Alternatively, alkyne 4b where LG is iodo is prepared by reaction of alkyne 3 with iodine, in the presence of triphenylphosphine and imidazole in a solvent such as ether, or acetonitrile, at a temperature of about 0° C. to room temperature for 8 to 24 hr. Alternatively, reaction of alkyne 3 with sodium iodide in acetone at room temperature from 8 to 36 hours affords substituted alkyne 4b where LG is iodo. Additionally, reaction of alkyne 3 with carbon tetrabromide in the presence of triphenylphosphine in tetrahydrofuran (THF) and the like at about 0° C. to about 35° C. for 8 to 72 hrs gives substituted alkyne 4c where LG is bromo.

Standard Pharmacological Test Procedures

The ability of the compounds of this invention to inhibit FPTase was evaluated in the standard pharmacological in vitro test procedures described below. Data for representative examples is summarized in Table I.

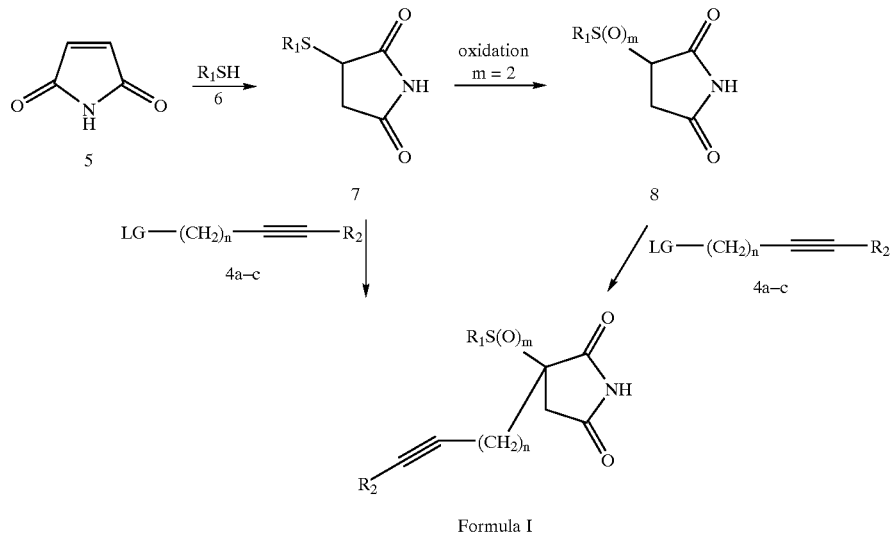

Referring to Scheme II, thiol 6 where $R_1$ is hereinbefore defined was reacted with maleimide 5 at about 0° to about 40° C. in a solvent selected from ethanol, and THF to give mercaptan 7. Optional oxidation of mercaptan 7 following the method of (Zask et al J. Med. Chem. 1990, 33, 1418–1423) using excess (2 to 20 equivalents) aqueous hydrogen peroxide in acetic acid at about 30° to about 80° C. for 1 to 10 h affords pyrrolidine-2,5-dione 8 where $R_1$ is hereinbefore defined and m is 2.

To a solution of pyrrolidine-2,5-dione 8 in tetrahydrofuran or N,N-dimethylformamide at room temperature to −78° C. was added two or more equivalents of a base which include but not limited to alkali metal hydrides such as sodium hydride, alkali metal alkyls such as butyl lithium or alkali metal amide bases such as lithium diisopropylamide or lithium bis(trimethylsilyl)amide. About two minutes to 1 hr after the addition of the base, one or more equivalents of substituted alkyne 4a–4c was added at 0° C. to room temperature and the reaction continued for 1 to 72 hrs to afford the 3-substituted-3-(substitutedsulfonyl)pyrrolidine-2,5-diones of Formula (I) where m is 2.

To a solution of mercaptan 7 in tetrahydrofuran or N,N-dimethylformamide at room temperature to −78° C. was added two or more equivalents of a base which include but not limited to alkali metal hydrides such as sodium hydride, alkali metal alkyls such as butyl lithium or alkali metal amide bases such as lithium diisopropylamide or lithium bis(trimethylsilyl)amide. About two minutes to 1 hr after the addition of the base, one or more equivalents of substituted alkyne 4a–4c was added at about 0° C. to room temperature and the reaction continued for 1 to 72 hrs to afford the 3-substituted-3-(substitutedsulfonyl)pyrrolidine-2,5-diones of Formula (I) where m is 0.

Enzyme test procedure: FPTase inhibition in vitro assay was performed according to James, G. L., Brown, M. S., and Goldstein, J. L., Methods in Enzymology, 1995, 255, 38–46; and Garcia, M. A., et al., J. Biol. Chem., 1993, 268, 18415–18420.

Materials—Purified FPTase (Moomaw, J. F. and Casey, P. J., J. Biol. Chem., 1992, 267, 17438–17443), purified $His_6$-Ras, inhibitor compounds at 10 mg/ml or 10 mM in 100% DMSO, $^3$H-FPP (50,000 dpm/pmol) Amersham, TCA/SDS (6%/2%), TCA (6%), Glass fiber filters (0.22–0.45 m), vacuum manifold or 96 well filtration plates.

Methods—1. Dilute FPTase inhibitors from stock solutions to 2.5× in 2.5% DMSO, 10 mM DTT, 0.5% octyl-B-glucoside. 2. Solution #1 is added to FPTase reaction in a volume of 20 ml. 3. Standard reaction mix, 50 ml, contains 50 mM Tris (7.5), 10 mM $ZnCl_2$, 3 mM $MgCl_2$, 20 mM KCl, 5 mM DTT, 0.2% octyl-B-glucoside, 1% DMSO, 40 mM $His_6$-Ras, 10 ng FPTase, and various concentrations of FPTase inhibitors. 4. Incubate for 30–90 min at 25° C. 5. Stop reactions with TCA/SDS (6%/2%), hold at 4° C. for 45–60 min. 6. Filter by manifold or 96 well plate, wash filter 3–5× with TCA (6%). 7. Add scintillant to filters, measure $^3$H-FPP incorporation into Ras protein.

Analysis of Results—Percent inhibition by test compounds is determined by the following:

(cpm from precipitated Ras with test compounds)−(background cpm)×100=% inhibition.

(cpm from precipitated Ras without test compounds)−(background cpm)

Cell-based test procedure: Tumor inhibition in vitro assay was performed according to P. Skehan, R. Storeng, D.

Scudiero, A. Monks, J. McMohan, D. Vistica, J. Warren, H. Bokesh, S. Kenney, and M. R. Boyd, *J. Natl. Cancer Instit.*, 1990, 82 (13), 1107–1112; L. V. Rubinstein, R. H. Shoemaker, K. D. Paull, R. M. Simon, S. Tosini, P. Skehan, D. A. Scudiero, A. Monks, and M. R. Boyd, *J. Natl. Cancer Instit.*, 1990, 82 (13), 1113–1118; A. Monks, et al., *J. Natl. Cancer Instit.*, 1991, 83, 757–766; M. R. Boyd and K. D. Paull, *Drug Development Res.*, 1995, 34, 91–109; and S. P. Fricker and R. G. Buckley, *Anticancer Research*, 1996, 16, 3755–3760.

Materials—Cell Lines: Human tumor cell lines DLD-1 and LoVo; ras-transformed rat fibroblast cell lines, RAT-H-ras and RAT-K-ras (growth inhibited by standard FPTase inhibitors), and the parent cell line RAT-2 (resistant to standard FPTase inhibitors). Cell Media: RPMI 1640 (or DMEM medium and McCoy's medium) with 10% Fetal Bovine Serum supplemented with L-glutamine and Pennicilin/Streptomycin. Compounds: Supplied usually as a 10 mM stock in 100% DMSO. Normal Saline: 150 mM NaCl Trichloroacetic Acid (TCA): 50% (w/v) in water. Sulforhodamine (SRB): 0.4% (w/v) in 1% Acetic Acid. Tris Base: 10 mM in water.

Methods—Cells are plated at 2000 cells per well, per 200 ml media, and allowed to adhere overnight at 37° C. At 24 h post plating, compounds are added directly at a volume of 0.5 ml. Compound is first diluted in DMSO to generate concentrations of compound or reference standard of: 1, 5, 10 and 25 mM. Dilutions can be made in an identical 96 well plate so that compounds can be added using a multichannel micropipettor set at 0.5 ml. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 ml of normal saline is then added to each well using an 8 well multichannel pipettor, followed by the careful addition of 50 ml of 50% TCA. The plates are then incubated for 2 h at 4° C., after which the supernatant is removed using the same technique as above and the plates washed twice with 200 ml water. The plates are then air dried and 50 ml of SRB stock solution is carefully added so that the entire bottom of each well is covered. This again can be used using an 8 well multichannel pipettor. The SRB is incubated with fixed cells for 15 min at room temperature, after which the SRB is removed with the manifold as described above and the plates washed twice with 350 ml of 1% acetic acid per well each time. The plates are then air dried after which the bound SRB is released from protein by the addition of 200 ml of Tris base. Resolubilizing the SRB is aided by placing the plates on a rotator for 15–30 min. The absorbance of each well is determined at 550 or 562 nm using a microtiter plate reader.

Analysis of Results—Each compound or dilution thereof is performed in triplicate. Outliers are identified by visual inspection of the data. Each plate should have a control (vehicle only). A standard curve is constructed by plotting the concentration of compound against the average absorbance calculated at that concentration. A curve is plotted and the concentration at which the curve passes through the 50% absorbance mark seen in the control well is the $IC_{50}$ calculated for that compound.

TABLE I in vitro FTase Inhibition Assay

| Compound | $IC_{50}$ H-Ras* $\mu M$ | $IC_{50}$ K-Ras* $\mu M$ |
|---|---|---|
| 3-[5-(4-Chlorophenyl)pent-4-ynyl]-3-(4-methoxybenzenesulfonyl)pyrrolidine-2,5-dione | 0.14 | >1.0 |
| 3-[3-(4-Chlorophenyl)prop-2-ynyl]-3-(4-methylbenzenesulfonyl)pyrrolidine-2,5-dione | 6.5 | |

*H-Ras or K-Ras used as substrates for farnesylation

Based on the results of these standard pharmacological test procedures, the compounds of this invention are useful as agents for treating, inhibiting or controlling ras-associated diseases, an in particular cancer, by inhibiting farnesyl-protein transferase enzyme, when administered in amounts ranging from about 10 to about 200 mg/kg of body weight per day. A preferred regimen for optimum results would be from about 10 mg to about 100 mg/kg of body weight per day and such dosage units are employed that a total of from about 100 mg to about 1000 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit.

For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

As used in accordance with this invention, the term providing an effective amount of a compound means either directly administering such compound, or administering a prodrug, derivative, or analog which will form an effective amount of the compound within the body.

The present invention further provides a method of treatment of ras oncogene-dependent tumors, such as cancers of the pancreas, colon, bladder, and thyroid; a method of controlling metastasis, suppressing angiogenesis, and inducing apoptosis; a method of treating Ras-associated proliferative diseases other than cancer, such as restenosis, neurofibromatosis, endometriosis, and psoriasis. The compounds of the present invention may also inhibit prenylation of proteins other than Ras, and thus provide a method of treatment of diseases associated with other prenyl modifications of proteins.

The invention will be more fully described in conjunction with the following specific examples which are not to be construed as limiting the scope of the invention.

The following nonlimiting examples further illustrate this invention:

REFERENCE EXAMPLE 1

5-(2,5-dichlorophenyl)pent-4-yn-1-ol

A solution of 1,4-dichloro-2-iodobenzene (20.0 g, 73.3 mmol), 4-pentyn-1-ol (6.17 g, 73.3 mmol), bistriphenylphosphine(Pd II) chloride (1.03 g, 1.47 mmol), and copper(I) iodide (0.14 g, 0.733 mmol) in 400 ml of diethylamine was stirred under nitrogen for three days. This was diluted with dichloromethane and the oily layer was adsorbed onto silica gel and eluted with hexanes-ethyl acetate (5:1) to give 5-(2,5-dichlorophenyl)-pent-4-yn-1-ol, 13.7 g (82%).

REFERENCE EXAMPLE 2

1-Chloro-4-(5-iodopent-1-ynyl)benzene 5-(4-Chlorophenyl)pent-4-yn-1-ol (35.7 g, 182 mmol), 4-dimetylamino-pyridine (8.9 g, 73 mmol), p-toluenesulfonyl chloride (34.7 g, 182 mmol), and 62 ml of triethylamine were combined in 330 ml of dichloromethane at 0° C. The mixture was stirred for 30 min. at 0° then 18 hours at room temperature. Dilution with 200 ml of dichloromethane followed by washing with brine, drying over magnesium sulfate, filtration through silica gel with hexane-ethyl acetate, 8:1, gave a yellow solid on evaporation. Crystallization from ether gave 5-(4-Chlorophenyl)pent-4-yn-1-ol p-toluenesulfonate as colorless crystals (31.7 g, 49% yield). This was converted to the title compound by reaction with sodium iodide in acetone, and was used in subsequent reactions with no further purification; MS m/z 303.9 (M+ calcd. for $C_{11}H_{10}CII=304.6$).

REFERENCE EXAMPLE 3

5-(4-Methanesulfonyl-phenyl)pent-4-yn-1-ol

Preparation of the title compound with 4-bromophenyl methyl sulphone (5.87 g, 25 mmol) and 4-pentyn-1-ol (2.1 g, 25 mmol) according to the procedure in Example 18 yielded 5.12 g (87%) of yellow oil which was characterized as 5-(4-Methanesulfonylphenyl)pent-4-yn-1-ol: NMR $(CDCl_3)$ δ 1.88–1.93 (m, 2H), 2.56–2.60 (t, J=6.99, 2H), 3.04 (s, 3H), 3.80–3.84 (t, J=6.15, 2H), 7.56 (d, J=5.1, 2H), 7.85 (d, J=4.8, 2H). MS m/z 239 (M+H cald. for $C_{12}H_{14}O_3S$ 238.3)

In a manner described in Reference Example 3 the following acetylenic alcohols in Table II were prepared from the corresponding iodobenzene or bromobenzene and 4-pentyn-1-ol (structures were confirmed as above by NMR):

TABLE II

| REFERENCE EXAMPLE | PRODUCT | Mass Spectrum M+ |
|---|---|---|
| 4 | 5-(2-Methyl-5-nitrophenyl)pent-4-yn-1-ol | 220 (M + H) |
| 5 | 5-(2-Methoxy-5-nitrophenyl)pent-4-yn-1-ol | 235.0 |
| 6 | 5-(2-Methoxy-4-nitrophenyl)pent-4-yn-1-ol | 235.0 |
| 7 | 5-(4-Nitro-2-trifluoromethyl-phenyl)pent-4-yn-1-ol | 273.0 |
| 8 | 5-(3-Fluoro-5-nitrophenyl)pent-4-yn-1-ol | 223.0 |
| 9 | 5-(3-Fluoro-4-methoxy-5-nitro-phenyl)pent-4-yn-1-ol | 254.2 (M + H) |
| 10 | 5-(4-Methoxy-2-nitrophenyl)pent-4-yn-1-ol | 234.2 (M + H) |

TABLE II-continued

| REFERENCE EXAMPLE | PRODUCT | Mass Spectrum M+ |
|---|---|---|
| 11 | 5-(2,5-Dimethyl-phenyl)pent-4-yn-1-ol | 189.1 (M + H) |
| 12 | 5-(5-Chloro-2-methylphenyl)pent-4-yn-1-ol | 208.8 (M + H) |
| 13 | 5-(4-Chloro-2-methylphenyl)pent-4-yn-1-ol | 208.0 |
| 14 | 5-(2,4-Dimethyl-phenyl)pent-4-yn-1-ol | 188.1 |
| 15 | 5-(2-Methyl-4-nitrophenyl)pent-4-yn-1-ol | 219.0 |
| 16 | 5-(4-Bromo-2-methylphenyl)pent-4-yn-1-ol | 253.0 |
| 17 | 3-(5-Hydroxypent-1-ynyl)-4-methylbenzoic acid methyl ester | 232.1 |
| 18 | 4-(5-Hydroxypent-1-ynyl)-3-methylbenzoic acid methyl ester | 232.1 |
| 19 | 5-(4-tert-Butylphenyl)pent-4-yn-1-ol | — |
| 20 | 5-(2-Chlorophenyl)pent-4-yn-1-ol | — |
| 21 | 5-(2,4-Dichlorophenyl)pent-4-yn-1-ol | — |
| 22 | 4-(5-Hydroxypent-1-ynyl)trifluoromethyl benzene | — |
| 23 | 4-(5-Hydroxypent-1-ynyl)trifluoromethoxy-benzene | — |
| 24 | 3-(5-Hydroxypent-1-ynyl)-4-methylbenzoic acid methyl ester | — |
| 25 | 5-(4-Chlorophenyl)pent-4-yn-1-ol | — |
| 26 | 5-(3-Chlorophenyl)pent-4-yn-1-ol | — |

REFERENCE EXAMPLE 27

3-(4-Phenoxy-phenyl)prop-2-yn-1-ol

Preparation of the title compound with commercial available 4-Bromodiphenyl ether (5.93 g, 23.8 mmol) according to the procedure in Reference Example 1 yielded 440 mg (8.2%) of brown oil which was characterized as 3-(4-phenoxyphenyl)prop-2-yn-1-ol: NMR (CDCl$_3$) δ 4.50 (d, J=6), 6.91 (d, J=2.01, 1H), 6.93 (d, J=2.01, 1H), 7.01 (d, J=0.63, 1H), 7.04 (d, J=1.17, 1H), 7.11–7.16 (m, 1H), 7.36 (d, J=0.6, 1H), 7.38 (d, J=2.52, 2H), 7.41 (d, J=1.92, 1H). MS m/z 224.08 (M+calcd. for C$_{15}$H$_{12}$O$_2$ 224.08)

REFERENCE EXAMPLE 28

3-Biphenyl-4-yl-prop-2-yn-1-ol

In a manner described in Example 1 above, propargyl alcohol was reacted with 4-bromobiphenyl to give the title compound as white crystals: NMR (CDCl$_3$) δ 4.53 (d, J=4.74, 2H), 7.38 (d, J=7.17, 1H), 7.42–7.60 (m, 8H). MS m/z 208 (M+ calcd. for C$_{15}$H$_{12}$O 208).

REFERENCE EXAMPLE 29

1-(3-Bromo-1-propynyl)-4-phenoxybenzene

A solution of 3-(4-Phenoxy-phenyl)-prop-2-yn-1-ol of Example 51 (415 mg, 1.85 mmol), triphenylphosphine (514 mg, 1.96 mmol), carbon tetrabromide (650 mg, 1.96 mmol) in THF (3 ml) was stirred at room temperature for 3 days. Evaporation of the solution, and chromatography of the residue gave the title compound as a brown oil:

NMR (CDCl$_3$) δ 4.16 (s, 2H), 6.91 (d, J=2.1, 1H), 6.93 (d, J=2.1, 1H), 7.01 (d, J=0.93, 1H), 7.04 (d, J=1.14, 1H), 7.12–7.17 (m, 1H), 7.36 (d, J=0.75, 1H), 7.39 (d, J=1.98, 2H), 7.42 (d, J=2.64, 1H). MS m/z 288 (M+1 calcd. for C$_{15}$H$_{11}$BrO 287.155)

REFERENCE EXAMPLE 30

1-Chloro-4-(5-iodopent-1-ynyl)benzene 5-(4-Chlorophenyl)pent-4-yn-1-ol (35.7 g, 182 mmol), 4-dimetylamino-pyridine (8.9 g, 73 mmol), p-toluenesulfonyl chloride (34.7 g, 182 mmol), and 62 ml of triethylamine were combined in 330 ml of dichloromethane at 0° C. The mixture was stirred for 30 min. at 0° then 18 hours at room temperature. Dilution with 200 ml of dichloromethane followed by washing with brine, drying over magnesium sulfate, filtration through silica gel with hexane-ethyl acetate, 8:1, gave a yellow solid on evaporation. Crystallization from ether gave 5-(4-Chlorophenyl)pent-4-yn-1-ol p-toluenesulfonate as colorless crystals (31.7 g, 49% yield). This was converted to the title compound by reaction with sodium iodide in acetone, and was used in subsequent reactions with no further purification; MS m/z 303.9.

REFERENCE EXAMPLE 31

1,4-Dichloro-2-(5-iodopent-1-ynyl)benzene 5-(2,5-Dichlorophenyl)pent-4-yn-1-ol (13.7 g, 59.8 mmol), triphenylphosphine (20.4 g, 77.8 mmol), and imidazole (5.71 g, 83.8 mmol) in a mixed solvent (100 ml acetonitrile-150 ml ether) was stirred under nitrogen at 0° C., and to this was slowly added iodine (21.3 g, 83.8 mmol). The solution was allowed to warm to room temperature and stirring was continued for 18 hours. This was chromatographed on silica gel with hexane to give the title compound (14.7 g, 72%), MS m/z 337.9 In the manner described in Example 30, above, the following alcohols in Table III were converted to the corresponding bromides:

TABLE III

| REFER. EXAMPLE | ALCOHOL | PRODUCT | MASS SPECTRUM |
|---|---|---|---|
| 32 | 5-(2,4-Dichlorophenyl)-pent-4-yn-1-ol | 1,5-Dichloro-2-(5-iodo-pent-1-ynyl)benzene | 337.9 |
| 33 | 5-(2-Methyl-5-nitro-phenyl)pent-4-yn-1-ol | 2-(5-Iodopent-1-ynyl)-1-methyl-4-nitro-benzene | 330 |
| 34 | 5-(2-Methoxy-5-nitro-phenyl)pent-4-yn-1-ol | 2-(5-Iodopent-1-ynyl)-1-methoxy-4-nitro-benzene | 345.1 |
| 35 | 5-(2-Methoxy-4-nitro-phenyl)pent-4-yn-1-ol | 1-(5-Iodopent-1-ynyl)-2-methoxy-4-nitro-benzene | 345.0 |
| 36 | 5-(4-Nitro-2-trifluoro-methyl-phenyl)pent-4-yn-1-ol | 1-(5-Iodopent-1-ynyl)-4-nitro-2-trifluoro-methylbenzene | 383.0 |
| 37 | 5-(3-Fluoro-5-nitro-phenyl)pent-4-yn-1-ol | 1-Fluoro-3-(5-iodo-pent-1-ynyl)-5-nitro-benzene | 334 |
| 38 | 5-(2,5-Dimethylphenyl)-pent-4-yn-1-ol | 1-(5-Iodopent-1-ynyl)-2,5-dimethyl-benzene | 298.0 |
| 39 | 5-(5-Chloro-2-methyl-phenyl)-pent-4-yn-1-ol | 4-Chloro-2-(5-iodopent-1-ynyl)-1-methyl-benzene | 317.9 |
| 40 | 5-(4-Chloro-2-methyl-phenyl)pent-4-yn-1-ol | 4-Chloro-1-(5-iodopent-1-ynyl)-2-methyl-benzene | 317.9 |
| 41 | 5-(2,4-Dimethyl-phenyl)pent-4-yn-1-ol | 1-(5-Iodopent-1-ynyl)-2,4-dimethyl-benzene | 298.0 |

TABLE III-continued

| REFER. EXAMPLE | ALCOHOL | PRODUCT | MASS SPECTRUM |
|---|---|---|---|
| 42 | 5-(2-Methyl-4-nitrophenyl)-pent-4-yn-1-ol | 1-(Iodopent-1-ynyl)-2-methyl-4-nitrobenzene | 328.9 |
| 43 | 5-(4-Bromo-2-methylphenyl)pent-4-yn-1-ol | 4-Bromo-1-(5-iodopent-1-ynyl)-2-methyl-benzene | 361.9 |
| 44 | 5-(2-Chlorophenyl)-pent-4-yn-1-ol | 1-Chloro-2-(5-iodopent-1-ynyl)benzene | 304.0 |
| 45 | 5-(2,4-Dichlorophenyl)-pent-4-yn-1-ol | 2,4-Dichloro-1-(5-iodo-pent-1-ynyl)benzene | 337.9 |
| 46 | 4-(5-Hydroxypent-1-ynyl)trifluoromethyl-benzene | 1-(5-Iodopent-1-ynyl)-4-trifluoro-methylbenzene | 337.9 |
| 47 | 4-(5-Hydroxypent-1-ynyl)trifluoromethoxy-benzene | 1-(5-Iodopent-1-ynyl)-4-trifluoro-methoxy-benzene | — |
| 48 | 5-(3-Nitrophenyl)pent-4-yn-1-ol | 1-(5-Iodopent-1-ynyl)-3-nitrobenzene | 315.8 |
| 49 | 5-(4-Nitrophenyl)pent-4-yn-1-ol | 1-(5-Iodopent-1-ynyl)-4-nitrobenzene | 315.9 |
| 50 | 5-(4-tert-Butylphenyl)pent-4-yn-1-ol | 1-tert-Butyl-4-(5-iodo-pent-1-ynyl)benzene | 326.0 |
| 51 | 5-(3-Chlorophenyl)pent-4-yn-1-ol | 1-Chloro-3-(5-iodo-pent-1-ynyl)benzene | 304.0 |
| 52 | 3-Biphenyl-4-ylprop-2-yn-1-ol | 4-(3-Bromoprop-1-ynyl)-biphenyl | 270 (M–H) |

EXAMPLE 1

3-[5-(4-Chlorophenyl)pent-4-ynyl]-3-(4-methoxybenzenesulfonyl)-pyrrolidine-2,5-dione To a solution of maleimide (5.92 g, 61 mmol) in 200 ml of ethanol was added 4methoxybenzenethiol (7.5 ml, 61 mmol), and after 18 hours at room temperature the solvent was removed to give 3-(4-methoxy-phenylsulfanyl) pyrrolidine-2,5-dione, mp 93–94° C. This compound (5.0 g, 21 mmol) was oxidized with hydrogen peroxide, 30% in acetic acid, 220 ml to give 3-(4-methoxybenzenesulfonyl) pyrrolidine-2,5-dione as a white solid, mp 144–146° C. This compound was reacted with 1-chloro-4-(5-iodopent-1-ynyl) benzene in DMF using two equivalents of sodium bishexamethyldisilazide to give the title compound as colorless crystals, mp 160–162° C.; mass spectrum,(M–H) 444.2.

EXAMPLE 2

3-[3-(4-Chlorophenyl)prop-2-ynyl]-3-(toluene-4-sulfonyl)pyrrolidine-2,5-dione

In a manner analogous to Example 1, there is obtained 3-(toluene-4-sulfonyl)pyrrolidine-2,5-dione, and this is reacted with 3-(4-chlorophenyl)prop-2-ynyl bromide (U.S. Pat. No. 5,605,918 Example 21) as in Example 1 to give the title compound as an off-white solid, mp 186–188° C.

EXAMPLE 3

3-[5-(2,5-Dichlorophenyl)pent-4-ynyl]-3-(4-methoxybenzenesulfonyl)-pyrrolidine-2,5-dione In a manner analogous to Example 1, and by the use of 1,4-dichloro-2-(5-iodopent-1ynyl)benzene there is obtained the title compound.

What is claimed is:
1. A process for the preparation of a compound of Formula (I).

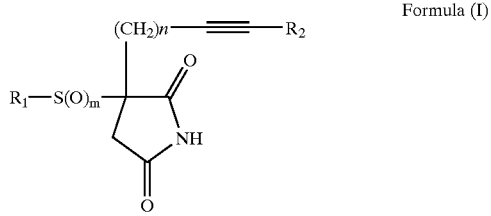

Formula (I)

wherein:
$R_1$ is a moiety

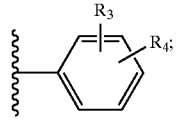

$R_2$ is a moiety

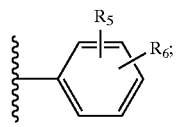

n is an integer of 1 and 3–9;
m is an integer of 0 or 2;
$R_3$ and $R_4$ are independently selected from the group consisting of hydrogen, alkyl of 1 to 10 carbon atoms, alkoxy of 1 to 10 carbon atoms, halogen, nitro, trifluoromethoxy, phenoxy optionally mono or di substituted, and benzyloxy optionally mono or di substituted;
$R_5$, and $R_6$, are independently selected from the group consisting of hydrogen, alkyl of 1 to 10 carbon atoms, halogen, nitro, phenyl optionally mono or di-substituted, phenoxy optionally mono or di-substituted, trifluoromethyl, trifluoromethoxy, and methanesulphonyl wherein mono or di-substitutents of phenyl, phenoxy, or benzyloxy are independently selected from the group consisting of alkyl of 1 to 10 carbon atoms, alkoxy of 1 to 10 carbon atoms, halogen, nitro, trifluoromethyl, trifluoromethoxy, methanesulphonyl, and phenyl;
or a pharmaceutically acceptable salt thereof,
which comprises
reacting a compound of the formula

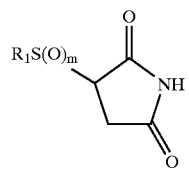

with an alkyne of the formula

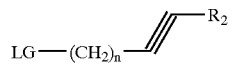

wherein LG is a leaving group
in the presence of a base to give a compound of Formula (I)
or a pharmaceutically acceptable salt thereof.

2. The process according to claim 1 wherein the base is selected from alkali metal hydrides, alkali metal alkyls and alkali metal amide bases.

3. The process according to claim 2 where the alkali metal hydride is sodium hydride.

4. The process according to claim 2 wherein the alkali metal alkyl is butyl lithium.

5. The process according to claim 2 wherein the alkali metal amide base is selected from lithium diisopropylamide and lithium bis(trimethylsilyl)amide.

6. The process according to claim 1 wherein the leaving group is p-toluenesulfonyloxy, iodo or bromo.

* * * * *